United States Patent [19]

El Hage

[11] Patent Number: 5,526,072
[45] Date of Patent: Jun. 11, 1996

[54] APPARATUS AND TECHNIQUE FOR AUTOMATIC CENTERING AND FOCUSING A CORNEAL TOPOGRAPHER

[75] Inventor: Sami G. El Hage, Houston, Tex.

[73] Assignee: Alcon Laboratories, Inc., Fort Worth, Tex.

[21] Appl. No.: 46,619

[22] Filed: Apr. 14, 1993

[51] Int. Cl.[6] .............................. A61B 3/107; A61B 3/15
[52] U.S. Cl. ......................... 351/208; 351/212; 351/221; 351/246
[58] Field of Search .................................. 351/206, 208, 351/212, 221, 216, 247, 200, 205

[56] References Cited

U.S. PATENT DOCUMENTS

| | | | |
|---|---|---|---|
| 3,248,162 | 4/1966 | Knoll | 351/212 |
| 3,432,227 | 3/1969 | Soper | 351/212 |
| 3,598,478 | 8/1971 | Townsley | 351/206 |
| 3,781,096 | 12/1973 | Townsley | 351/212 |
| 3,797,921 | 3/1974 | Kilmer et al. | 351/206 |
| 3,937,566 | 2/1976 | Townsley | 351/247 |
| 4,019,813 | 4/1977 | Cornsweet et al. | 351/212 |
| 4,569,576 | 2/1986 | Karpov et al. | 351/212 |
| 4,662,730 | 5/1987 | Outwater et al. | 351/212 |
| 4,685,140 | 8/1987 | Mount, II | 382/6 |
| 4,692,003 | 9/1987 | Adachi et al. | 351/212 |
| 4,761,071 | 8/1988 | Baron | 351/212 |
| 4,772,115 | 9/1988 | Gersten et al. | 351/212 |
| 4,863,260 | 9/1989 | Gersten et al. | 351/212 |
| 4,881,807 | 11/1989 | Luce et al. | 351/208 |
| 4,902,123 | 2/1990 | Yoder, Jr. | 351/212 |
| 4,978,213 | 12/1990 | El Hage | 351/212 |
| 4,995,716 | 2/1991 | Warmicki et al. | 351/212 |
| 5,009,498 | 4/1991 | Gersten et al. | 351/212 |
| 5,018,850 | 5/1991 | Gersten et al. | 351/212 |
| 5,062,702 | 11/1991 | Bille | 351/212 |
| 5,106,183 | 4/1992 | Yoder, Jr. | 351/212 |
| 5,159,361 | 10/1992 | Cambier et al. | 351/212 |
| 5,212,505 | 5/1993 | Penney | 351/247 X |
| 5,214,456 | 5/1993 | Gersten | 351/212 |
| 5,300,965 | 4/1994 | Kitajima | 351/212 |
| 5,307,096 | 4/1994 | Baroth et al. | 351/212 |

OTHER PUBLICATIONS

Klyce, Stephen D.; "Computer-Assisted Corneal Topography"; *Investigative Ophthalmology & Visual Science*; vol. 25, Dec. 1984, pp. 1426–1435.
Fundamentals of Corneal Topography, brochure by EyeSys Technologies, 1992.
TMS–1 Topographic Modeling System brochure by Tomey Technology, Inc. 1992.

*Primary Examiner*—William L. Sikes
*Assistant Examiner*—David R. Parsons
*Attorney, Agent, or Firm*—Jeffrey S. Schira

[57] ABSTRACT

A corneal topographer including a directional light source, a CCD and a positioning stage all controlled by a computer for automatically centering and focusing the corneal image onto the CCD. The computer receives video signals from the CCD representing the corneal image, which is digitized and displayed on a real-time basis on a monitor screen. A reflection of the directional light source is positioned to align in the center of the corneal image. An operator moves an optics head to place the corneal image on the monitor screen, roughly focuses the image, and then commands the computer to take over. The computer calculates the distance between the image of the directional light source and the center of the CCD, and activates the positioning stage to move the directional light source image to the center. The positioning stage is moved within a focusing range, where several positions and corresponding intensity characteristics of the directional light source image are tabulated. A best fit algorithm calculates the maximum intensity characteristic corresponding to the maximum focus, and the computer moves the optics head to a position corresponding to maximum focus.

16 Claims, 4 Drawing Sheets

APPARATUS AND TECHNIQUE FOR AUTOMATIC CENTERING AND FOCUSING A CORNEAL TOPOGRAPHER

BACKGROUND OF THE INVENTION

1. Field of the Invention

The present invention relates to an apparatus and method for automatically centering and focusing a corneal image on a detection array of a corneal topographer.

2. Description of the Related Art

Photokeratoscopes, and more recently, corneal topographers, are used to determine the contour of the cornea of the human eye, thus facilitating the design and fitting of contact lenses as well as for use in the performance of surgical procedures.

For example, contact lenses are fitted on the basis of the measurement of the central corneal curvature using a keratometer or an ophthalmometer. It is thus necessary to select lenses from different trial sets until the "quasi" appropriate one is found. This is a tedious procedure that requires a long time and a wide variety of trial cases. Contact lenses, thus fitted, require various modifications after they are ordered from the laboratory to be adapted to each cornea. Because of imprecision of the geometry and poor quality of the finished lenses, some patients could not tolerate them. If a contact lens is to be designed on the spot and without a return trip of the patient, there is a need for permitting the images to be processed and a determination to be made as quick as possible.

Corneal topographers allow data to be processed more efficiently, which is urgently needed in the performance of certain surgical procedures. One such surgical procedure is known as radial keratotomy, where microincisions are placed on the cornea in an attempt to surgically modify the curvature of the cornea, and thereby reduce or eliminate myopia or astigmatism. Thus, the accuracy of this procedure depends to some degree on the ability to measure the original shape of the cornea. Improvements on corneal topographer instrumentation is invaluable in continuing to increase the accuracy of radial keratotomy or refractive surgery.

Corneal topography apparatus is also useful in myopic and hyperopic keratomileusis in which the corneal curvature is altered to improve refractive error by removal of the corneal "disc" predicted thickness with a microkeratome. Corneal transplantation is performed for scarred or diseased corneas by replacing optically inferior cornea with clear tissue. Sutures are placed strategically so that the tissue heals in the most spherical fashion without astigmatism. Corneal topography apparatus is further useful in intraocular removal of a cloudy lens and subsequent replacement of an intraocular lens, wherein, after entering the eye, the wound and sutures are manipulated so as to reduce astigmatism. Corneal topography provides the surgeon with information how to close the wound and how to calculate the power of the intraocular lens.

In conventional photokeratoscopes used for measuring the contour of the cornea, concentric rings of light from a source of light within a housing are directed onto a cornea and reflected by the cornea onto the film of a camera as an image of the rings. The deviation of the rings from their known concentricity can be measured on the film and this data processed mathematically to determine the actual contour of the cornea, which of course, is not a perfect sphere and which differs from one individual to another. Conventional photokeratoscopes are disclosed in U.S. Pat. Nos. 3,248,162 and 3,598,478.

In use of apparatus of this type, the cornea of an individual to be examined is located in a position having its optical axis at least approximately aligned with the axis of the target of rings and the lens of the camera. The deviation of this optical axis from alignment can then be determined. Although the calculations for determining its contour do not require absolute alignment, it is desirable that it be as closely aligned as possible in the interest of a more accurate determination. In order to avoid relocating the cornea of the individual to be examined, and to bring the axis of the images rings into substantial alignment with the optical axis of the eye, the target and optical system of the camera are preferably adjustable with respect to the chin rest. French Patent No. 7122413 shows a photokeratoscope in which such adjustment may be made by a "joy stick" conventionally located for use by the operator of the photokeratoscope.

A corneal topographer is disclosed in U.S. Pat. No. 4,978,213, which provides significant improvements over prior photokeratoscopes used for corneal measurements. The corneal topographer or the '213 patent generally includes a housing including an apparatus for providing illuminated rings for reflection off the cornea. Camera means, such as a charge-coupled-device (CCD) camera system, is included for sensing the images of rings of light reflected from the cornea. The camera apparatus sends standard video signals to a computer including a conventional, off-the-shelf image processor, which digitizes the video signals. The computer analyzes the digital data and produces data useful in determining a contour of the cornea of the human eye. Positioning means, preferably comprising step motors, is provided for manually positioning the corneal topographer to receive accurate measurements.

The effectiveness and accuracy of the measurements taken from a corneal topographer is directly dependent upon the accuracy of the positioning of the apparatus relative to the cornea. The correct mapping of the eye depends directly upon the centered image, since misalignment of the equipment results in skewed measurements, and thus inaccurate mapping and calculations. If the image is misaligned, the corneal contour may not be accurately determined, leading to erroneous diagnosis in surgical procedures or fitting lenses. It is further recognized that an unfocused image increases error in the corneal data measurements. The better the focus, the more accurate the measurements and the better the diagnosis can be made from those measurements.

It has been discovered that manual focusing and centering by an operator is inherently inaccurate and time consuming. The level of accuracy and typically varies from one operator to the next, and also on the amount of care used by any given operator. Operator error is particularly problematic since it is based on upon subjective judgment which varies from one operator to the next and even with the same operator over time. Also, even an experienced operator of corneal topographers must adjust and readjust the image to achieve proper centering and focusing. Meanwhile, the patient must remain as still as possible, since even slight eye movements requires readjustment by the operator. Manual positioning has proved to be a tedious and frustrating experience, especially with a fidgety patient.

Thus, it is desirable to substantially reduce the amount of time required for, and operator error typically resulting from, manually positioning corneal topography equipment. Improvements in the accuracy of the corneal measurements will improve the diagnosis based upon those measurements.

SUMMARY OF THE PRESENT INVENTION

A corneal topographer apparatus according to the present invention automatically centers and focuses a corneal image reflected from a patient's cornea onto a charge-coupled-device (CCD) camera system. The patient is positioned, preferably using a chin rest, opposite an optics head for receiving the corneal image. The optics head projects concentric rings of light to the cornea, which reflects the corneal image through a center hole of the optics head onto a planar surface or screen of the CCD. A point of light source, preferably comprising a light emitting diode (LED), is also projected to the cornea in the center of the ring pattern, and then reflected from the cornea to the CCD.

The optics head is mounted to a positioning stage for moving the optics head relative to the cornea. The positioning stage preferably includes step motors for maneuvering the optics head in the X, Y and Z directions for centering and focusing purposes. A computer system is included for controlling the optics head and the positioning stage. The CCD camera system converts the corneal image into standard video signals, which are transmitted to the computer system for processing and for display. The computer system includes an image processor for converting the video signals into digital form for storage and display. A monitor screen attached to the computer system is provided for displaying the corneal image in real time. The computer system scans, stores and analyzes the digitized corneal images from the CCD, and then controls the motors for moving the positioning stage to center and focus the corneal image on the CCD. The computer system includes an input device, such as a keyboard, mouse or the like, so that the operator can manually control the corneal topographer or initiate routines for automatically centering and focusing as described below.

The operator first manually positions the positioning stage until the concentric rings are displayed on the monitor screen, and then roughly focuses the image. The operator then instructs the computer system to execute software for automatically centering and focusing the image. The computer turns on the LED to nearly its brightest level, and then digitizes and stores the corneal image. The LED is then turned off and another image is digitized and stored while the LED remains off. The computer compares and subtracts the two images, resulting in a differential image containing information corresponding to the location of the LED. The differential image is scanned for the LED image, and the position of the LED image relative to the center of the CCD is calculated and stored.

The distance is then converted into step counts, which are the number of steps that the X and Y step motors must make to move the optics head to properly center the corneal image. The frequency at which the step motors operate preferably depends upon the distance to be moved. Thus, the greater the distance, the faster the step motors are moved. The step motors are advanced more slowly as the distance gets smaller, thus reducing vibrations at the head of the patient, which would otherwise interfere with valid image acquisition. After the step motors are moved, the entire process is repeated until the differential image reveals that the LED image is at the center of the CCD. The operator may terminate the procedure at any time.

The operator manually focuses the image if not already done, and then indicates to the computer system to initiate automatic focusing. The computer first turns off the light source illuminating of the rings leaving the LED image, and then moves the optical head in the Z axis a predetermined range on either side of the manual focus point. Several incremental corneal images are scanned for the LED image, where the position of the optics head and an intensity characteristic of the LED image is determined and stored. The greatest intensity characteristic corresponds to the highest focal point. In this manner, a table of optics head positions and corresponding LED intensity characteristics are created. The intensity characteristic values are then analyzed to determine the brightest, clearest and narrowest LED image. Preferably, a best fit algorithm is then utilized to calculate the position corresponding to the highest LED intensity characteristic. The computer then moves the optics head to the position corresponding to the maximum intensity characteristic.

It is appreciated that the automatic centering and focusing technique and apparatus according to the present invention provides a much quicker and more accurate method for determining the contour of the cornea of a patient. The apparatus is positioned much quicker, and operator error is significantly reduced, so that accurate measurements may be taken in a consistent manner.

BRIEF DESCRIPTION OF THE DRAWINGS

A better understanding of the present invention can be obtained when the following detailed description of the preferred embodiment is considered in conjunction with the following drawings, in which.

DETAILED DESCRIPTION OF THE PREFERRED EMBODIMENT

Figure 1:
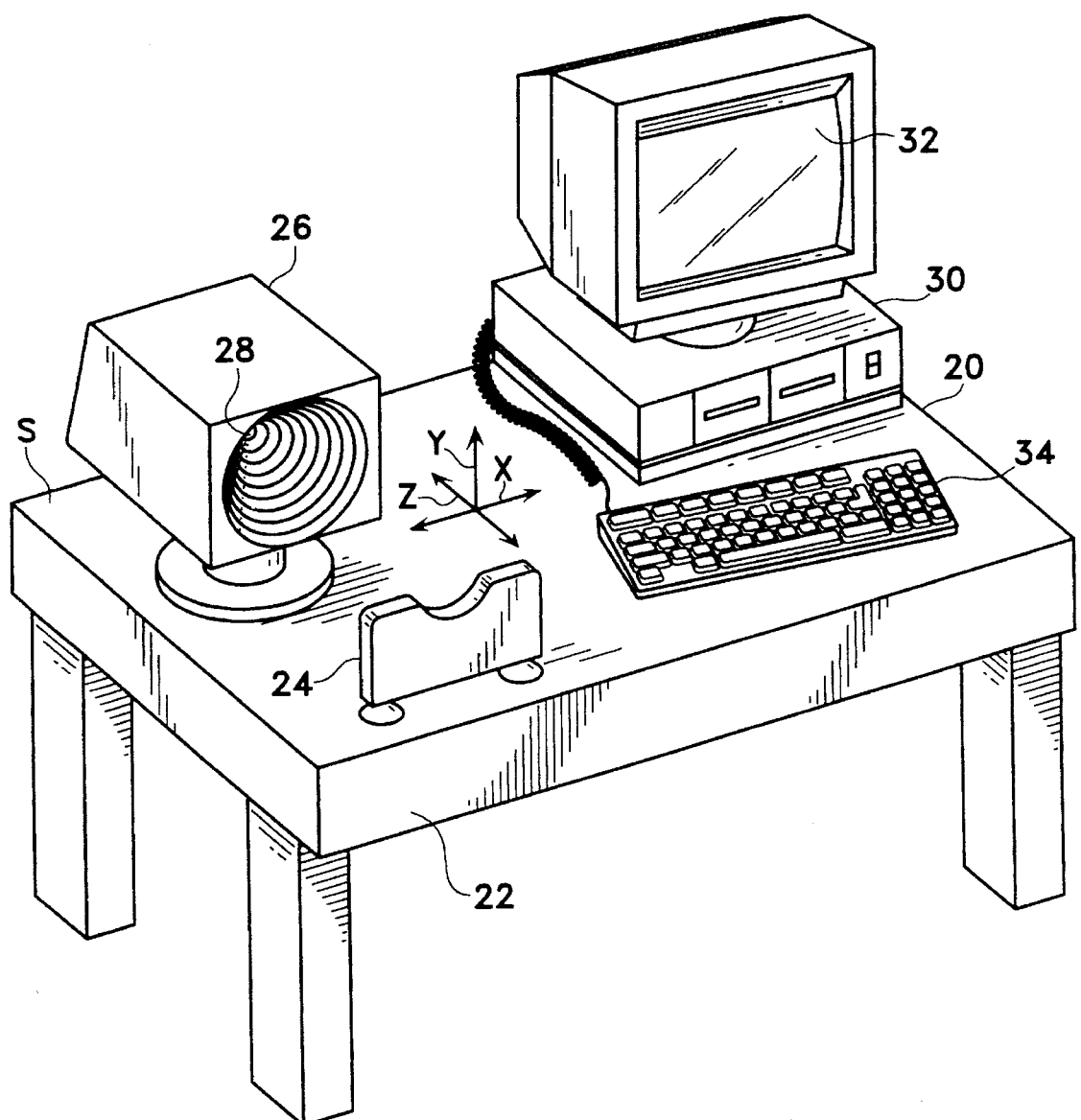
FIG. 1 is a perspective view of a corneal topographer apparatus incorporating the automatic centering and focusing technique according to the present invention.

Referring now to FIG. 1, a perspective view is shown of a corneal topographer including the automatic centering and focusing capability according to the present invention. A table 20 is shown which is preferably used for holding and containing the apparatus according to the present invention, although other suitable means could be used for housing the equipment. The table 20 includes a horizontal surface S convenient for supporting certain portions of the apparatus, and a cabinet portion 22 for holding certain control portions as further described below. A chin rest 24 is preferably located or mounted on the surface S of the table 20 for conveniently locating the cornea C (FIG. 2) of an individual for examination purposes. An optics head 26 is placed above the surface S opposing the chin rest 24 for purposes of examination of the cornea C. As will be described more fully below, the optics head 26 transmits concentric rings of light, which are reflected off the cornea C of the patient back through a center hole 28 of the optics head 26 and received by a charged-coupled-device (CCD) 54 (FIG. 2).

The optics head 26 preferably mounted above the surface S is operably connected to a positioning stage 60 (FIG. 2) mounted within the cabinet portion 22 of the table 20. The positioning stage 60 preferably includes motors, described below, for moving the optics head 26 relative to the patient in three axes of movement, generally referred to as the X axis, the Y axis and the Z axis, respectively, as shown in FIG. 1. Preferably, the X axis defines movement left and right, the Y axis defines movement up and down and the Z axis towards and away relative to the cornea C. Thus, the X and Y axes preferably define a plane of movement perpendicular to the optic axis of the cornea C, in which plane the optics head 26 is moved for purposes of centering. The Z axis is preferably in a direction of movement parallel to the optic axis of the cornea C, in which axis the optics head 26 is moved for purposes of focusing. The motor apparatus for moving the optics head 26 will be described more fully below, but is generally controlled by a computer 30. A monitor screen 32 and a keyboard 34 are connected to the computer 30, which are all conveniently located on the surface S of the table 20.

Figure 2:
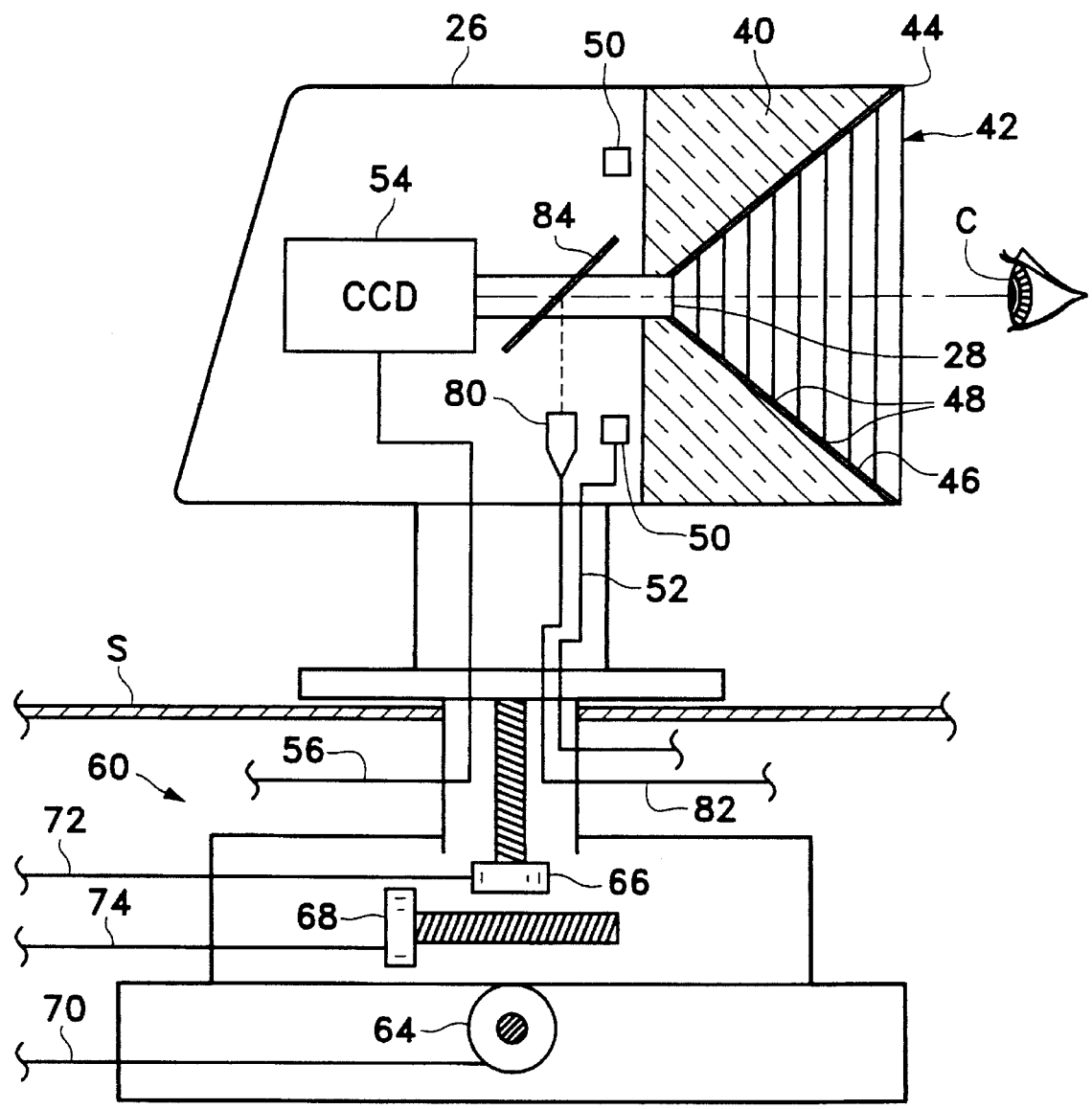
FIG. 2 is a sectional side view of the corneal topographer of FIG. 1.

Referring now to FIG. 2, a sectional side view of the optics head 26 is shown above the surface S of the table 20. Attached to the positioning stage 60 positioned below the surface S. The optics head 26 preferably incorporates a target 40 comprising a body of transparent material, such as hard plastic, having a frusto conically shaped opening 42 with an open, large end 44 opposing the cornea C of the patient. The inner surface 46 of the opening 42 of the target 40 is covered with an opaque material, which is interrupted along its length to form coaxial slits 48, through which rings of light are transmitted onto the cornea C of the patient. A light source 50, preferably comprising a singular circular light or a series of equally spaced lamps arranged in a circle adjacent the rear portion of the target 40 within the optics head 26, projects light through the target 40 and the coaxial slits 48 to form the concentric rings of light. The light source 50 is connected to the computer 30 through a signal line 52, so that the computer 30 can turn on and off the light source 50.

The cornea C of the patient to be examined is located with its optical axis approximately aligned with the axis of the coaxial slits 48 and the center hole 28. The CCD 54 is preferably located at the end of the center hole 28 opposite the cornea C for receiving the reflected corneal image reflected from the cornea C through the center hole 28. The CCD 54 preferably converts the corneal image into standard video signals, which are then transmitted across a video cable 56 to the computer 30 for processing. The computer 30 preferably includes a standard image processor for receiving the video signals from the CCD 54, converting the video signals to digital form and temporarily storing the digital signals into a frame buffer. The frame buffer preferably comprises digital memory representing one frame or full screen, where the frame buffer is constantly updated with new data received from the CCD 54. The digital data is displayed on the monitor screen 32, preferably on a real-time basis, although some delay may be interposed. In this manner, the operator of the corneal topographer is capable of viewing the reflected corneal image in near real-time. Also, each frame may be stored in the main memory of the computer system 30. In the preferred embodiment, the CCD 54 is mapped onto the monitor screen 32 on a pixel by pixel basis, where a common center point or center pixel of the CCD 54 is mapped to a corresponding memory location within the frame buffer, which preferably corresponds to the center of the CCD 54. The monitor screen 32 may encompass the entire CCD 54 or a portion thereof.

The positioning stage 60 is designed in a similar manner as that described in U.S. Pat. No. 4,978,213, mentioned above, which is hereby incorporated by reference. In general, the positioning stage 60 includes a first reversible motor 64 for moving the optics head 26 in the X axis direction, a second reversible motor 66 for moving the optics head 26 along the Y axis and a third reversible motor 68 for moving the optics head 26 along the Z axis. The motors 64, 66 and 68 are preferably step motors receiving pulses or commands for incremental angular displacement, to permit incremental adjustments of the optics head 26 in the X, Y and Z axes. Each motor 64, 66 and 68 are individually operated to permit each adjustment to be made independently of each other. Other means would also be included, such as journals, lead screws, follower blocks and guide rods as generally described in the U.S. Pat. No. 4,978,213 used in conjunction with the motors 64, 66 and 68 for movement of the optics head 26. The motors 64, 66 and 68 are controlled using electrical signals provided from the computer 30 through electrical connections or signal lines 70, 72 and 74, respectively. In this manner, the operator of corneal topographer can press a key on the keyboard 34, or enter commands by any other input device, to manipulate the optics head 26 in the X, Y and Z directions.

A directional light source, preferably comprising a high-intensity light-emitting diode (LED) 80, is mounted within the optics head 26 for reflection off the cornea C of the patient. It is understood that other light sources and directional means could be used instead of the LED 80. The LED 80 is connected to and controlled by the computer 30 through an electrical connection or signal line 82. The LED 80 may thus be turned on an various intensity levels or otherwise turned off by the computer 30.

Preferably, the light of the LED 80 is directed towards a reflector 84 positioned to reflect the light from the LED 80 along the center axis of the center hole 28 towards the cornea C. The reflector 84 is preferably located between the cornea C and the CCD 54 behind the center hole 28, so that the center axis of the center hole 28 passes through a common point defined by the intersection of the light from the LED 80 with the reflector 84. The LED 80 is preferably mounted so that its light is directed perpendicular to and intersecting the center axis, whereas the reflector 84 is preferably mounted at an angle to reflect the light from the LED 80 at the intersecting point along the center line of the center hole 28. The reflector 84 is preferably mounted at a 45° angle relative to the center line of the center hole 28. Thus, the LED 80 projects a locator beam of light onto the reflector 84, so that the reflection of light from the LED 80 is aligned at the center of the concentric rings of light. The locator beam of light from the LED 80 is also reflected off the cornea C and back to the CCD 54. In this manner, if the locator light beam from the LED 80 strikes the apex or center of the cornea C, it is reflected back to the center point of the CCD 54. The image formed on the CCD 54 from the LED 80 and reflected by the cornea will be referred to as the LED image.

The operator of the corneal topographer turns on the light source 50 and views the monitor screen 32 to determine if the center of the corneal image appears on the monitor screen 32. If not, the operator sends commands through the keyboard 34 to move the optics head 26 until the center of the corneal image can be seen on the monitor screen 32. It is noted that the corneal image appears generally as concentric rings having the LED image in the center. Further, the operator views the patient relative the optics head 26 and can quickly align the optics head 26 so that the corneal image appears on the monitor screen 32. The operator may then move the optics head 26 along the Z axis for roughly focusing the image. It takes an appreciable amount of time for the operator to attempt an accurate center and focus, so that manual centering and focusing in this manner is inaccurate and time-consuming. Instead, the operator issues a command at the keyboard 34 to execute a software program which completes the centering and focusing process automatically. As described below, the video signals representing the corneal image from the CCD 54 are analyzed by the computer 30, which then activates the motors 64, 66 and 68 to accurately center and focus the corneal image onto the CCD 54, and thus onto the monitor screen 32 for diagnosis.

Figure 3:
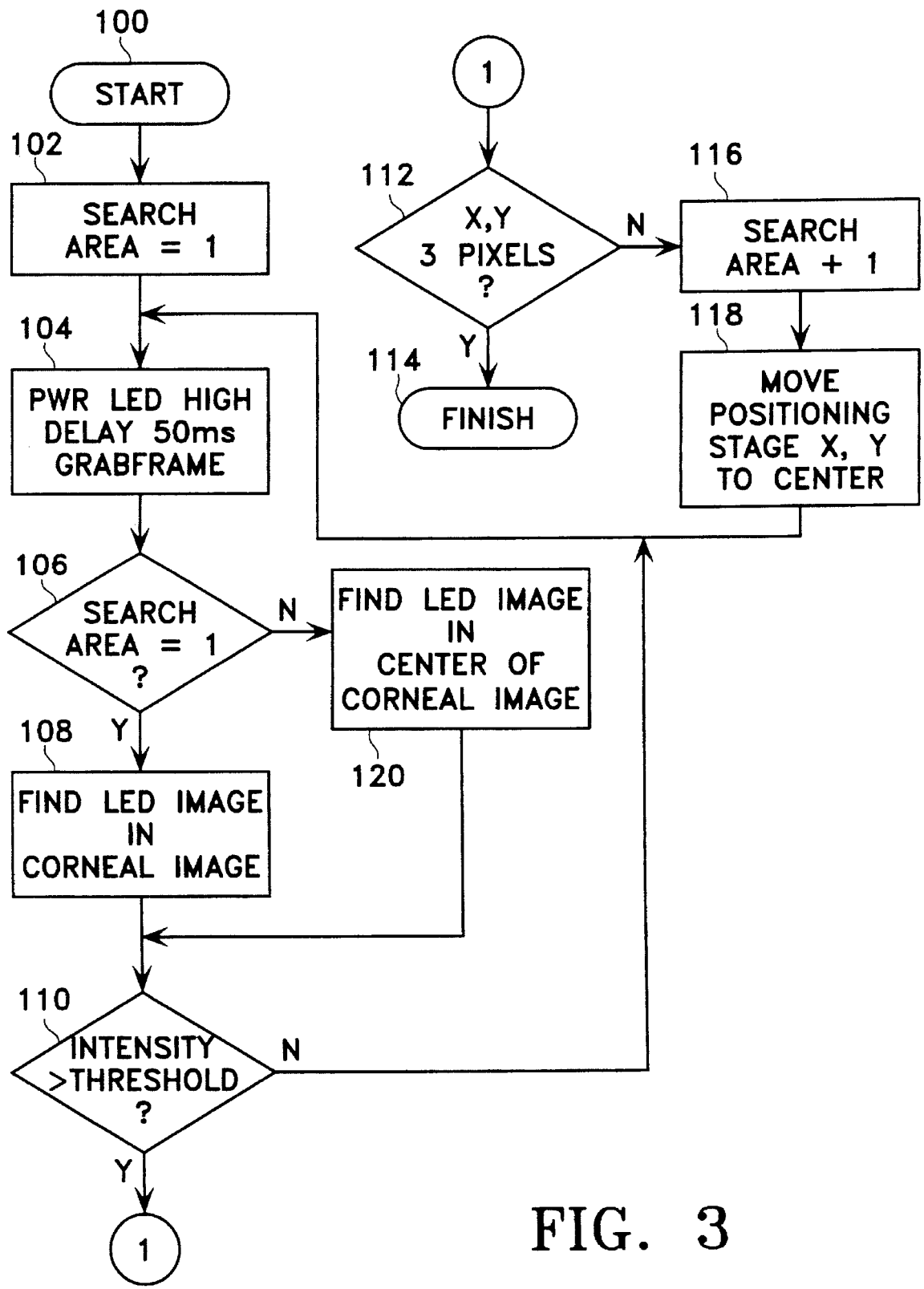
FIG. 3 is a flowchart diagram illustrating operation of an automatic centering routine executed by the computer of FIG. 1.

Referring now to FIG. 3, a flowchart diagram is shown illustrating the operation of a centering routine executed by the computer 30. Operation begins at step 100 and proceeds to step 102, where a flag referred to as SEARCH AREA is set equal to 1. Operation then proceeds to step 104 where the LED 80 is turned full on or at a high intensity level. A delay of preferably approximately 50 milliseconds (ms) is inserted to assure that the LED 80 has reached its full intensity level. The digital data in the frame buffer is then stored in the computer 30 as indicated by a command GRABFRAME.

A signal is sent on signal line 82 to turn the LED 80 off and another video image from the CCD 54 contained in the frame buffer is stored in the computer 30. Thus, two stored images are now contained within the memory of the computer 30 comprising essentially the same image with and without the LED image. The two stored images are then digitally subtracted resulting in a differential image which contains digitized information of the LED 80 alone, since all other common elements of the two pictures have been removed. The differential image is then stored. Alternatively, the light source 50 is shut off while the LED 80 remains on to obtain the differential image. This alternative method is not preferred because it is relatively time consuming. Operation then proceeds to step 106 where the SEARCH AREA flag is queried to determine if it is equal to 1. If so, which is the case during the first iteration of the centering routine, operation proceeds to step 108 where the entire differential image is read or scanned to locate the brightest point, which is the LED image representing the relative position of the optics head 26 relative to the cornea C. The scanning procedure locates an area of the differential image having a relatively high intensity representing the LED image. The distance, preferably in pixels on the CCD 54, between the LED image and the center of the CCD 54 is then measured and converted into step counts. It is noted that for purposes of simplicity, the memory locations in the frame buffer corresponding to the center of the CCD 54 and the LED image are used to calculate the distance. Although the cornea is spherical it is assumed planar for purposes of calculating the distance, so that there is preferably a one to one correspondence between distances on the cornea C and the CCD 54. The step counts represent the number of steps in the X and Y directions that the motors 64 and 66 must make to move the optics head 26 to properly center the reflection from the cornea C onto the CCD 54.

Referring back to step 106, after the first iteration of the routine, the SEARCH AREA flag will no longer be equal to 1 so that operation proceeds from step 106 to step 120. Step 120 is similar to step 108 except that only the small area at the center of the differential image corresponding to the center of the CCD 54 is read or scanned for locating the LED image. Step 120 saves time since after the first iteration the entire image need not be re-scanned since the LED image is located relatively close to the center of the CCD 54.

From steps 108 or 120, operation proceeds to step 110, where the intensity of the LED image is compared to a certain threshold value. This step assures that the image from the LED 80 is present, which would not be the case if the patient blinks thus removing the LED image. If the LED image is not present, operation proceeds back to step 104 to repeat. Otherwise, if the intensity of the LED image is greater than the threshold value indicating its presence, operation proceeds to step 112 where the distance between the LED image and the center of the CCD 54 is compared to a certain maximum distance in both the X and Y directions. The direction is measured in pixels, where the maximum distance is preferably 3 pixels. Thus, if the LED image is within 3 pixels in both the X and Y directions, operation is considered complete and the routine exits at step 114. Upon first iteration, this will generally not be the case unless the manual focus was arbitrarily accurate in the first place.

If the LED image is not properly centered, operation proceeds to step 116 from step 112 where the SEARCH AREA flag is incremented. Operation then proceeds to step 118 where the motors 64 and 66 are advanced by the number of step counts determined in steps 108, 120, to move the optics head 26 and relocate the LED image in the center of the CCD 54. In the preferred embodiment, the computer 30 sends commands or current pulses on the signal lines 70, 72 and 74 to advance the motors 64, 66 and 68 through incremental angular displacements. The speed of the motors 64, 66 and 68 is controlled by the frequency of the commands or pulses, where delays between successive commands or pulses operate to slow the motors 64, 66 and 68. The greater the distance between the LED image and the center of the monitor screen 32, the faster the motors 64 and 66 are moved. Conversely, if the distance between the LED image and the center of the CCD 54 is relatively small, the motors 64 and 66 are moved more slowly by inserting delays between successive commands. This procedures reduces vibrations at the head of the patient, which would otherwise interfere with valid image acquisition. After the optics head 26 is moved by the number of steps determined in either steps 108 or 120, operation proceeds back to step 104 to repeat the entire process.

Once the LED image is located within the maximum distance as indicated in step 112, operation completes in step 114. In step 112, or in a similar step preferably added, it is queried whether a termination command is indicated from the keyboard 34 as entered by the operator to terminate the centering of the corneal image. Alternatively, this termination command may be implemented as an interrupt. Thus, the operator of the corneal topographer can terminate the centering procedure at any time during operation.

Figure 4:
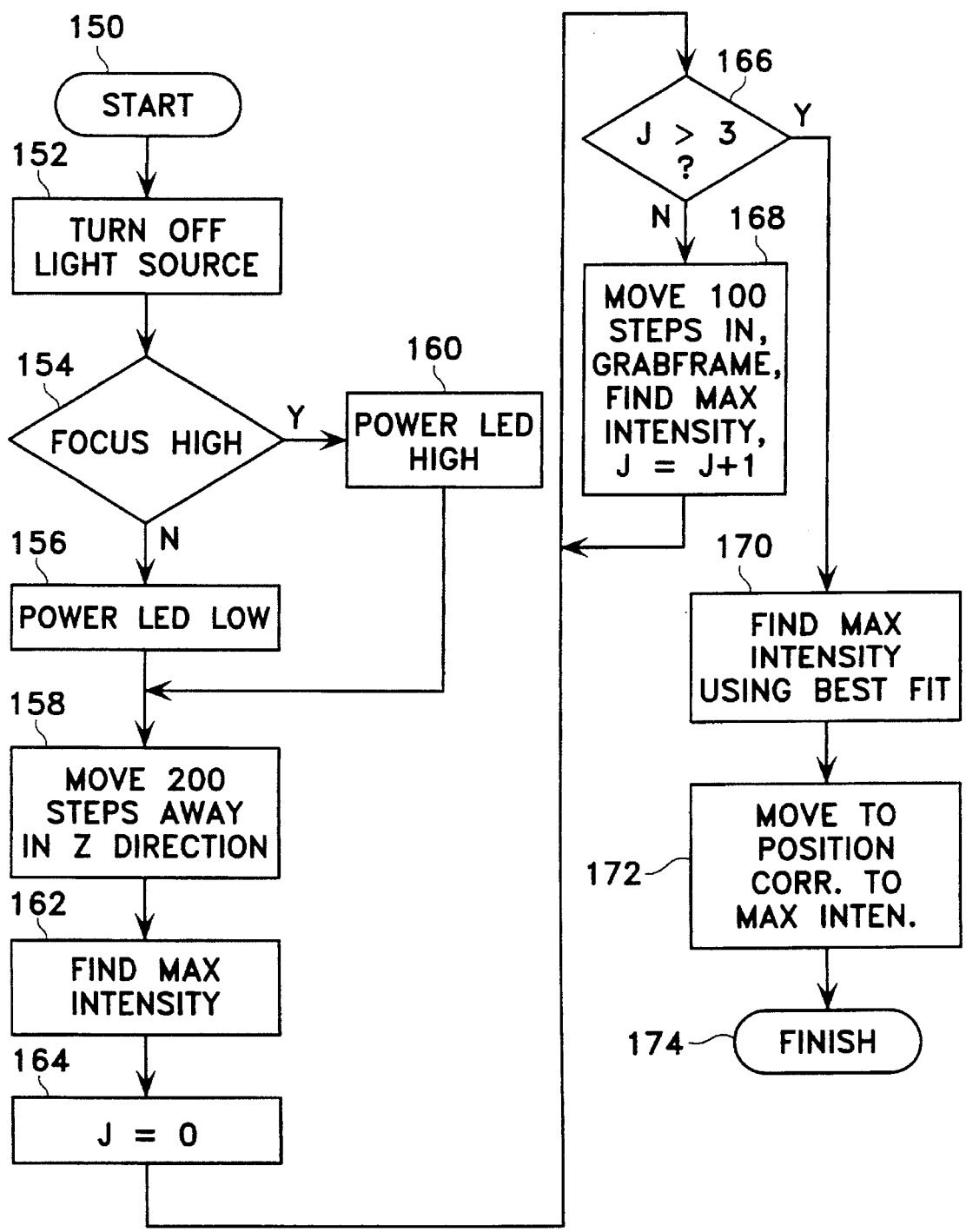
FIG. 4 is a flowchart diagram illustrating operation of an automatic focusing routine executed by the computer of FIG. 1.

Referring now to FIG. 4, a flowchart is shown illustrating operation of an automatic focusing routine according to the present invention executed by the computer 30. Before the focus routine in FIG. 4 is executed, the image should preferably be roughly focused by the operator, which typically occurs before the centering routine. The focusing routine is preferably executed immediately after the centering routine. The computer 30 may automatically execute the focus routine following the centering routine, or the computer 30 could pause or prompt the operator for initiating the focusing routine by entering a command. In the preferred embodiment, the operator may enter commands to initiate the centering and focusing routines individually, or to initiate both where the centering routine is executed first.

Operation of the focus routine begins at step 150 and proceeds to step 152, where the light source 50 is turned off. Only the LED image is necessary for automatic focusing purposes. Operation proceeds to step 154 to determine whether the focus is desired high or low. Focus low is used for calibration purposes, where a high reflective surface, such as a steel ball or other reflective surfaces, is used instead of the cornea C. Since the model typically reflects a majority of light, the LED 80 is turned on low. The cornea C generally reflects a small proportion of light, such as approximately 1%, so that the LED 80 must be turned on high. If desired low for calibration, operation proceeds to step 156 where the LED 80 is powered on low to reduce its intensity. Operation then proceeds to step 158 from step 156. If the focus is desired high for measuring the cornea C, operation proceeds from step 154 to step 160 where the LED 80 is powered on high and then operation proceeds to step 158. In step 158, the motor 68 receives commands or pulses from the computer 30 to move the optics head 26 a certain predetermined distance in a direction away from the cornea C of the patient. This predetermined distance preferably corresponds to 200 steps of the motor 68, although it is understood that other distances may be used. It has been determined that 200 steps corresponds to an appropriate distance on either side of the manual focus point to form a range for locating an optimum focus position of the optics head 26.

After the optics head 26 is moved away from the cornea C the predetermined distance, the entire frame is digitized and stored as well as the position of the optics head 26 relative to the initial position. Operation then proceeds to step 162, where a small area of the center of the stored image is scanned for the LED image, where this small area is preferably 20 pixels in length and width. When the LED image is found, characteristics of the intensity of the LED image, such as width, clarity and the peak intensity, are calculated and stored with the position of the optics head 26. These characteristics will generally be referred to as the intensity characteristic, which represents the relative focus of the LED image corresponding to the focus of the corneal image. The greater the intensity characteristic, corresponding to the brightest, clearest and narrowest LED image, the greater the focus.

Operation then proceeds to step 164, where an iteration count integer J is set equal to 0, and then proceeds to step 166, where J is compared to 3. If J is not greater than 3, operation proceeds to step 168 where the optics head 26 is moved towards the cornea C a certain distance, which preferably corresponds to 100 steps of the motor 68. The corneal image is then scanned for the LED image, and the intensity characteristic is calculated and stored along with the corresponding position of the optics head 26. The iteration flag J is then incremented and operation proceeds back to step 166. When J is greater than 3 as determined in step 166, operation proceeds to step 170. Thus, a table is established with two values per entry, including the position of the optics head 26 versus the intensity characteristic of the LED image. In this manner, four iterations of step 168 are performed, so that five different entries are made in the table. The set of intensity characteristics are analyzed together using a best fit algorithm to find the particular position where the intensity characteristic of the LED image is a maximum. It is noted that since only five positions are used, the maximum focus point is likely to be at an intermediate point between two of the five positions. Once the best fit algorithm is executed on the intensity values, operation proceeds to step 172 where the optics head 26 is moved to the position corresponding to the maximum intensity. Operation then is completed at finish step 174.

It is understood that the distance on either side of the manual focus point defining the focus range, the number of video images and whether the optics head 26 is first moved towards or away from the cornea C are merely design variable or considerations, which could change depending upon the particular apparatus. Also, if the number of intensity characteristic measurements is increased enough, such as 20 or 30 or more, the best fit algorithm may not be necessary. In that case, the position corresponding to the highest intensity characteristic measured would be chosen as the maximum focus point. Also, steps 166 and 168 could be placed in a sub-routine and executed again using a smaller focal distance to further enhance the accuracy of the focus.

In summary, the corneal topographer of the preferred embodiment includes a CCD and a reflected and centered directional light source image for centering and focusing purposes. A positioning stage allows a computer to maneuver the optics head 26 in X, Y and Z directions to achieve the optimal position of the optics head relative to the cornea. The corneal images from the CCD are digitized and stored in the computer. Software calculates the distance between the directional light source image and the center of the CCD, and activates the motors to center the corneal image. The intensity characteristic of the directional light source image is compared a several positions, and a best fit algorithm is used to find the optimum focal point.

It can now be appreciated that a corneal topographer apparatus according to the present invention automatically centers and focuses a corneal image onto a CCD, substantially increasing accuracy and decreasing operator errors. The execution of the centering and focusing routines occur very quickly and much more accurately then can be achieved by an operator attempting to center and focus the image manually. Once the corneal image is properly centered and focused, it provides a very accurate determination of the topography of the cornea C.

Although the invention has been described with reference to its preferred embodiments, those of ordinary skill in the art may, upon reading this disclosure, appreciate changes and modifications which do not depart from the scope and spirit of the invention as described above or claimed hereafter.

I claim:

1. A corneal topographer for determining the contour of the cornea, comprising:

an optics head, including:
  a light source,
  means directing said light source as a plurality of concentric rings of light toward the cornea, said concentric rings of light having a common axis,
  means for transmitting a locator beam of light towards the cornea along a center line coaxial with said common axis for said concentric rings of light said means including a directional light source and a means located between a charge-coupled device and the cornea for reflecting the light from the directional light source towards the cornea, and
  the charge-coupled device, which detects a corneal image reflected by the cornea, being mounted with said optics head for movement therewith, said charged-coupled device having a center point, the corneal image including a center image from said locator beam of light, and for converting the corneal image to video signals;

a positioning assembly operatively connected to said optics head for moving said optics head in a plane perpendicular to the optical axis of the cornea; and a computer coupled to said charge-coupled device, said light source and said positioning assembly, including:
  means for converting said video signals representing said corneal image from said charge-coupled device to digital data, means for reading the digital data representing the corneal image and for locating the center image from said locator beam of light, means for determining the distance between said center image and the center point of said charge-coupled device, and means for sending commands to said positioning assembly to move the optics head so that the corneal image detected by the charge-coupled device moves the distance determined by the determining means towards the center point of said charge-coupled device.

2. The corneal topographer of claim 1, wherein said directional light source comprises a high-intensity light emitting diode.

3. The corneal topographer of claim 1, wherein said directional light source transmits light perpendicular to and intersecting said center line coaxial with the concentric rings of light, and wherein said means for reflecting is located to intersect and reflect light from said directional light source at a point of intersection with said center line.

4. The corneal topographer of claim 1, wherein said positioning assembly includes:

a first step motor operatively connected to said optics head for moving said optics head along an X axis in the plane perpendicular to the axis of the cornea; and a second step motor operatively connected to said optics head for moving said optics head along a Y axis in the plane perpendicular to the axis of the cornea.

5. The corneal topographer of claim 1, wherein said positioning assembly further includes means for moving said optics head along a Z axis parallel to the optical axis of the cornea.

6. The corneal topographer of claim 5, wherein said means for moving said optics head along the Z axis comprises a step motor.

7. The corneal topographer of claim 5, wherein said computer further includes:

means coupled to said converting means for storing the digital data;

wherein said command sending means sends commands to move said optics head within a focal range along said Z axis; and wherein said storing means stores a plurality of corneal images within said focal range.

8. The corneal topographer of claim 7, wherein said computer further includes means coupled to said reading means for calculating an intensity characteristic for the center image of the corneal image.

9. The corneal topographer of claim 8, wherein said intensity characteristic calculating means calculates a plurality of intensity characteristics, and wherein said storing means stores said plurality of intensity characteristics and positions along the Z axis corresponding to the plurality of digitized and stored corneal images.

10. The corneal topographer of claim 8, wherein said computer further includes means for determining a maximum intensity characteristic from the plurality of intensity characteristics using a best fit algorithm.

11. The corneal topographer of claim 10, wherein said command sending means sends commands to move said optics head along the Z axis to a position corresponding to said maximum intensity characteristic.

12. An apparatus for automatically focusing the corneal image received by an optics head of a corneal topographer, wherein the optics head has a center line generally aligned with the optical axis of a cornea being examined, comprising:

means for moving the optics head along a Z axis parallel with the center line;

means for transmitting a beam of light along the center line of the optics head towards the cornea;

means for detecting an image of the beam of light reflected from the cornea, and for converting the detected image into video signals;

means for converting the video signals to digital data;

processing means receiving said digital data and controlling said moving means, said processing means comprising:

means for moving the optics head along said Z axis within a focus range;

means for digitizing and storing a plurality of detected images within said focus range;

means for reading said digitized and stored images and for calculating a corresponding intensity characteristic for each of said detected images;

means for determining a maximum intensity characteristic from said intensity characteristics; and wherein said moving means moves the optics head to a position on the Z axis corresponding to the maximum intensity characteristic.

13. A method of centering a corneal image reflected from a cornea onto a charged-coupled device of a corneal topographer, where the charge-coupled device and a directional light source are located in a movable optics head and where the charge-coupled device has a predetermined center point, comprising the steps of:

projecting light from the directional light source to form a directional light source image in the center of the corneal image;

continually detecting and converting the reflected corneal image to digital data;

reading the digital data to locate the directional light source image relative to the predetermined center point;

calculating the distance between the directional light source image and the predetermined center point;

moving the optics head so that the directional light source is moved towards the predetermined center point by the calculated distance;

moving the optics head to a plurality of discrete positions within a focal range along a Z axis, where the Z axis is parallel with an optical axis of the cornea;

storing a digitized data set representing a corneal image for each discrete position, and also storing a number representing the position of the optics head corresponding to each digital data set for each discrete position;

reading the digitized corneal images and calculating an intensity characteristic of the directional light source image corresponding to each of the stored positions of the optics head;

calculating a maximum intensity characteristic based on the plurality of maximum intensity characteristics: and moving the optics head to a position on the Z axis corresponding to the maximum intensity characteristic.

14. The method of claim 13, after said calculating step, further comprising the step of comparing the calculated distance to a predetermined maximum distance.

15. The method of claim 14, wherein said detecting, reading, calculating, comparing and moving steps are repeated until the calculated distance is less than the predetermined maximum distance.

16. A method of focusing a corneal image reflected from a cornea onto a charge-coupled device located within an optics head of a corneal topographer, where the corneal image includes a centered directional light source image, comprising the steps of:

moving the optics head to a plurality of discrete locations within a focal range along a Z axis parallel with the optical axis of the cornea;

detecting and converting the reflected corneal image at each of the discrete location to a digital data set;

storing the digital data sets and the corresponding position of the optics head;

calculating an intensity characteristic of the centered directional light source image for each stored digital data set;

calculating a maximum intensity characteristic based on the intensity characteristics; and moving the optics head to a position along the Z axis corresponding to the maximum intensity characteristic.

* * * * *